US00PP33614P2

(12) United States Plant Patent
Hartman

(10) Patent No.: US PP33,614 P2
(45) Date of Patent: Nov. 2, 2021

(54) ***CALADIUM* PLANT NAMED 'RFL THAI OF13-1055'**

(50) Latin Name: ***Caladium* X *hortulanum***
Varietal Denomination: RFL THAI OF13-1055

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/121,626

(22) Filed: Dec. 14, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — C. Anne Whealy

(57) ABSTRACT

A new and distinct cultivar of *Caladium* plant named 'RFL THAI OF13-1055', characterized by its tall and upright to somewhat mounding plant habit; dense and bushy appearance; vigorous growth habit and rapid growth rate; fancy-type leaves that are dark green and reddish brown in color with random deep pink-colored spots and flecks and dark purple-colored venation and petioles that are dark brown to almost black in color.

8 Drawing Sheets

Figure 1:
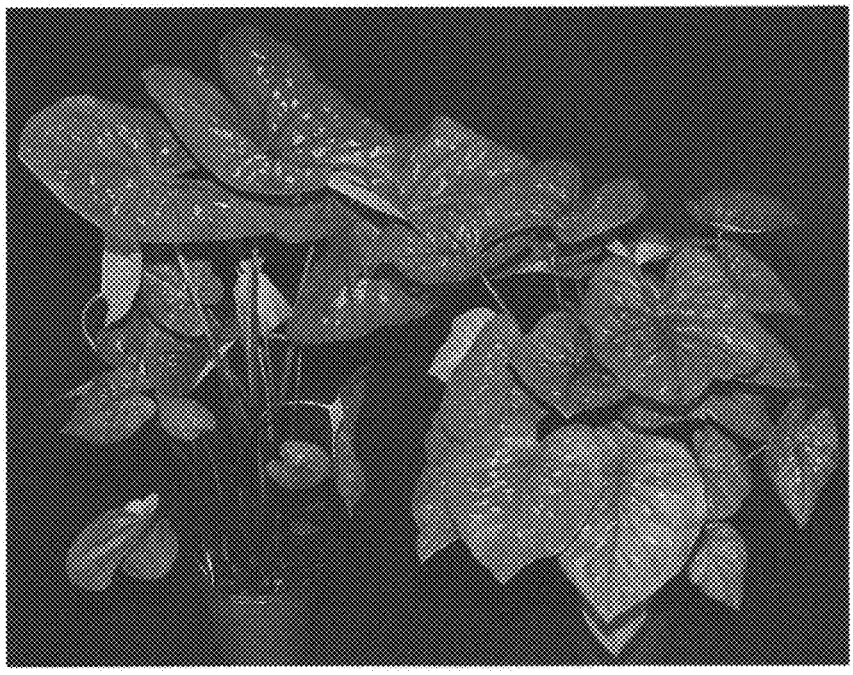

Botanical designation: *Caladium* X *hortulanum*.
Cultivar denomination: 'RFL THAI OF13-1055'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'RFL THAI OF13-1055'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Red Flash', not patented, as the female, or seed, parent with *Caladium* X *hortulanum* 'Thai 4', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RFL THAI OF13-1055'. These characteristics in combination distinguish 'RFL THAI OF13-1055' as a new and distinct *Caladium* plant:

1. Tall and upright to somewhat mounding plant habit; dense and bushy appearance.
2. Vigorous growth habit and rapid growth rate.
3. Fancy-type leaves that are dark green and reddish brown in color with random deep pink-colored spots and flecks and dark purple-colored venation.
4. Petioles that are dark brown to almost black in color.

Plants of the new *Caladium* differ primarily from plants of the female parent, 'Red Flash', in leaf color as leaves of the new *Caladium* are dark green and reddish brown in color with random deep pink-colored spots and flecks and dark purple-colored venation whereas leaves of 'Red Flash' have red-colored venation and interveinal areas with pink and white-colored spots and dark green-colored borders. In addition, plants of the new *Caladium* differ from plants of 'Red Flash' in leaf petiole color as plants of the new *Caladium* have dark brown to almost black-colored leaf petioles whereas plants of 'Red Flash' have reddish pink to tannish pink-colored leaf petioles with dark stripes.

Plants of the new *Caladium* differ primarily from plants of the male parent, 'Thai 4', in the following characteristics:

1. Plants of the new *Caladium* are larger, are more vigorous and grow faster than plants of 'Thai 4'.
2. Plants of the new *Caladium* are more freely branching when than plants of 'Thai 4'.
3. Plants of the new *Caladium* and 'Thai 4' differ in leaf color as leaves of the new *Caladium* are dark green and reddish brown in color with random deep pink-colored spots and flecks and dark purple-colored venation whereas leaves of 'Thai 4' are bronze red in color with random pink-colored spots and almost black-colored venation.

Plants of the new *Caladium* can be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in leaf color as leaves of the new *Caladium* are dark green and reddish brown in color with random deep pink-colored spots and flecks and dark purple-colored venation whereas leaves of 'Burning Heart' are bronze red in color with contrasting salmon orange-colored spots and dark red bronze-colored venation. In addition, plants of the new *Caladium* differ from plants of 'Burning Heart' in leaf petiole color as plants of the new *Caladium* have dark brown to almost black-colored leaf petioles whereas plants of 'Burning Heart' have tan and green-colored leaf petioles.

Plants of the new *Caladium* also can be compared to plants of *Caladium* X *hortulanum* 'John Peed', not patented. In side-by-side comparisons, plants of the new *Caladium* differ primarily from plants of 'John Peed' in the following characteristics:

1. Plants of the new *Caladium* grow faster than plants of 'John Peed'.
2. Plants of the new *Caladium* and 'John Peed' differ in leaf color as leaves of the new *Caladium* are dark green and reddish brown in color with random deep pink-colored spots and flecks and dark purple-colored venation whereas leaves of plants of 'John Peed' have red-colored centers and red-colored venation with olive green-colored margins.
3. Plants of the new *Caladium* and 'John Peed' in leaf petiole color as leaf petioles of the new *Caladium* are dark brown to almost black in color whereas leaf petioles of 'John Peed' are dark pink in color with dark green to almost black-colored streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a comparison view of typical plants of 'RFL THAI OF13-1055' grown in containers, the plant on the left has not had its tuber de-eyed and the plant on the right has had its tuber de-eyed prior to planting.

Figure 2:
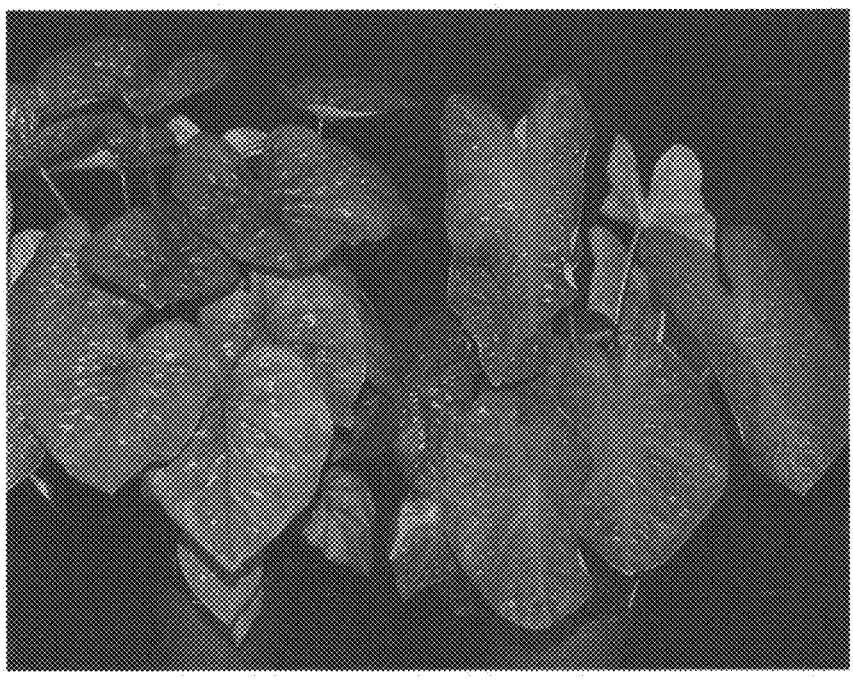

The photograph on the second sheet (FIG. 2) is side perspective view of 'RFL THAI OF13-1055' (left) and the female parent, 'Red Flash' (right).

Figure 3:
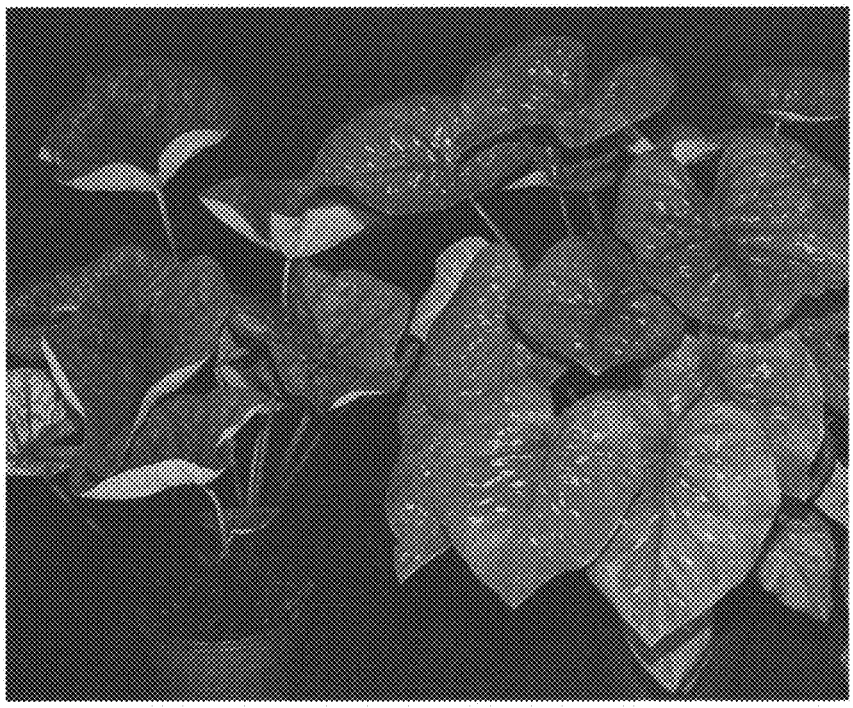

The photograph on the third sheet (FIG. 3) is side perspective view of the male parent, 'Thai 4' (left) and 'RFL THAI OF13-1055' (right).

Figure 4:
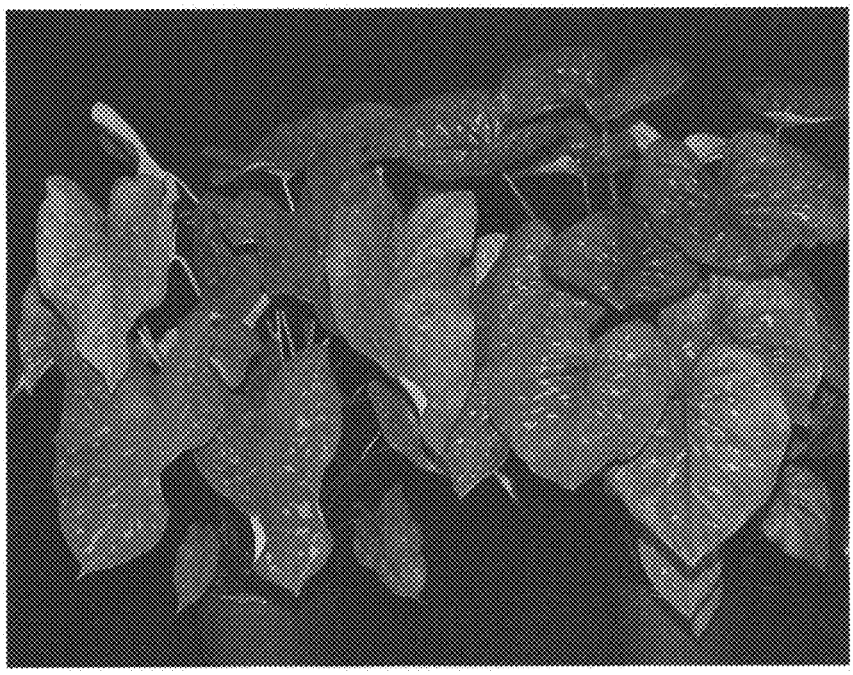

The photograph on the fourth sheet (FIG. 4) is a comparison view of typical potted plants of 'Burning Heart' (left) and 'RFL THAI OF13-1055' (right).

Figure 5:
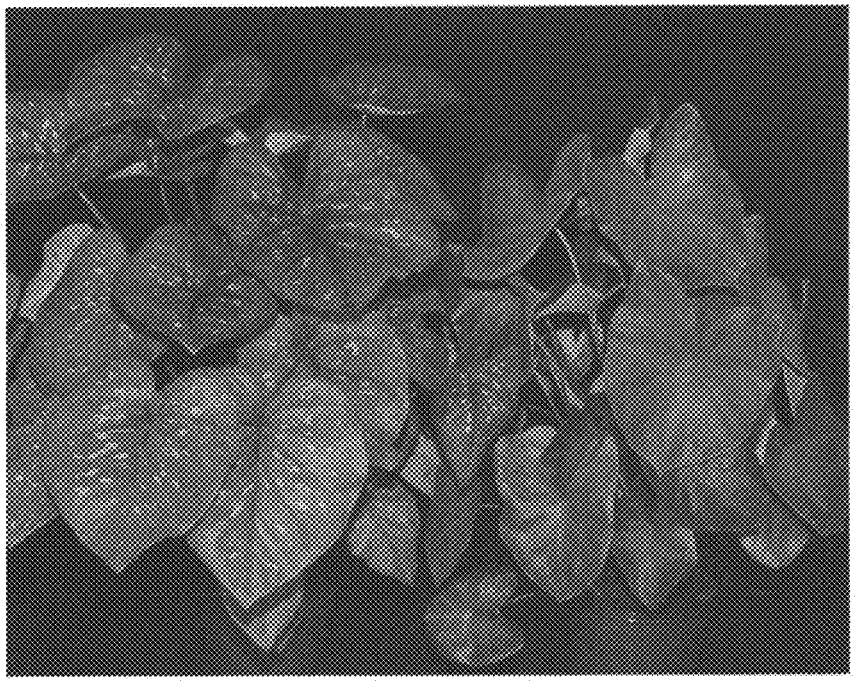

The photograph on the fifth sheet (FIG. 5) is a comparison view of typical potted plants of 'RFL THAI OF13-1055' (left) and 'John Peed' (right).

Figure 6:
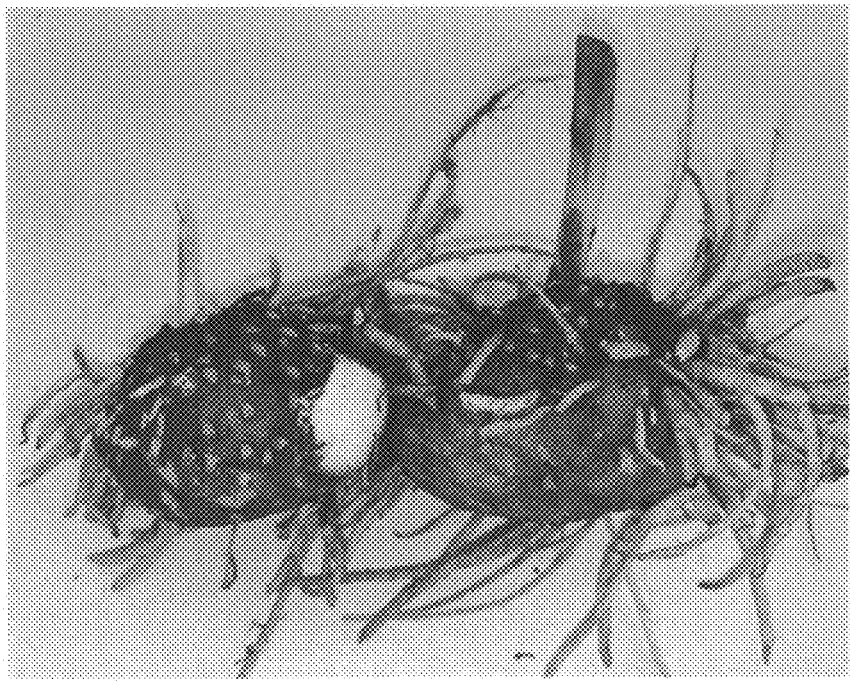

The photograph on the sixth sheet (FIG. 6) is a close-up view of typical freshly-harvested tubers with roots and leaf petioles of 'RFL THAI OF13-1055'.

Figure 7:
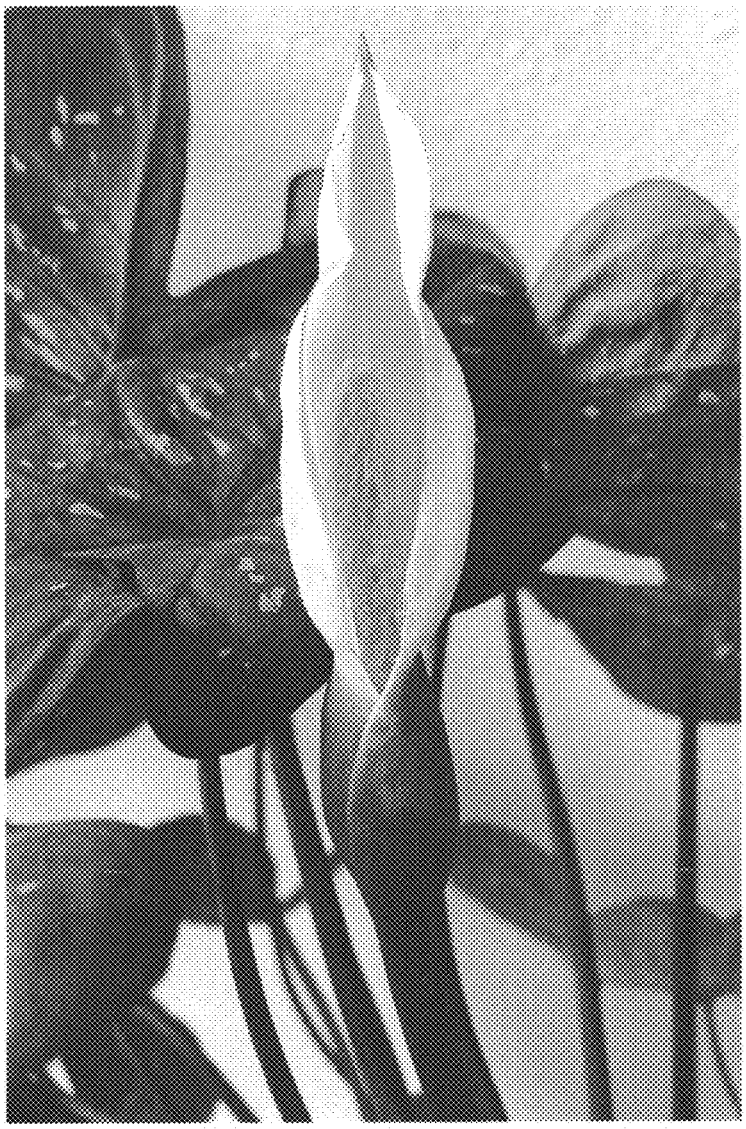

The photograph on the seventh sheet (FIG. 7) is a close-up view of a typical inflorescence of 'RFL THAI OF13-1055'.

Figure 8:
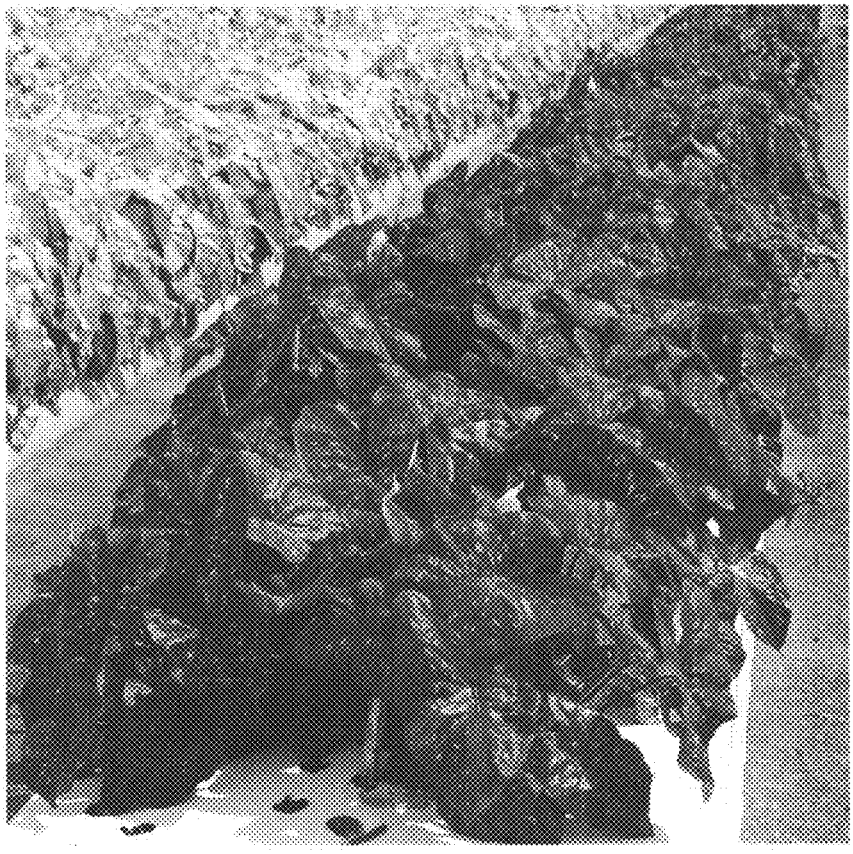

The photograph on the eighth sheet (FIG. 8) is a side perspective view of typical plants of 'RFL THAI OF13-1055' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were twelve weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'RFL THAI OF13-1055'.

Parentage:

*Female, or seed, parent.*—*Caladium* X *hortulanum* 'Red Flash' not patented.

*Male, or pollen, parent.*—*Caladium* X *hortulanum* 'Thai 4', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments are large and elliptic in shape. Height: About 4.5 cm. Diameter: About 5.9 cm to 9.8 cm. Segment height: About 2.2 cm to 3.7 cm. Segment diameter: About 2.4 cm to 5.9 cm. Axillary bud shape: Roughly triangular. Axillary bud size: About 5 mm by 6 mm.

Texture: Thick, starchy; somewhat brittle. Color: Periderm, freshly-harvested: Close to 199A. Periderm, dried: Close to 200A. Epidermis: Close to 159A and 177D; when developing, close to 179D. Cortical tissue: Close to 2C and 2D. Axillary buds: Close to 54D tinged with close to N186A.

*Root description*.—Thick, fleshy contractile roots with few lateral branches; color, close to NN155D.

*Rooting habit*.—Very dense.

Plant description:

*Plant type*.—Herbaceous perennial; suitable as a potted plant in containers 15-cm to 25-cm and suitable as a landscape plant in shaded areas.

*Plant and growth habit*.—Tall and upright to somewhat mounding plant habit; dense and bushy appearance; vigorous growth habit and rapid growth rate; potted plants finish in saleable form in about four to six weeks after planting tubers; leaf petioles and leaves arise from one or more growing points on tubers; leaf petioles initially upright and leaning outwardly with development.

*Plant height, from soil level to top of foliar plane, shade house-grown potted plants*.—When tubers are de-eyed, about 44 cm to 53 cm; tubers not de-eyed, about 65 cm to 76 cm.

*Plant height, from soil level to top of floral plane, shade house-grown potted plants*.—When tubers are de-eyed, about 44.5 cm.

*Plant diameter or spread, shade house-grown potted plants*.—When tubers are de-eyed, about 57 cm to 60 cm; tubers not de-eyed, about 60 cm to 76 cm.

*Number of shoots per plant, shade house-grown potted plants, tubers de-eyed*.—About eight to ten develop per #1 tuber.

*Number of shoots per plant, shade house-grown potted plants, tubers not de-eyed*.—About two to three develop per #1 tuber.

*Cataphylls, shade house-grown potted plants*.—Length: About 6.7 cm to 10 cm. Width: About 1.7 cm to 2.1 cm. Shape: Lanceolate to elliptic. Apex: Variable, obtuse to emarginate. Base: Sheathing the stein. Color: Outer surface: Close to 182D densely stippled and streaked with close to between 200A and N200A or may be entirely close to 202A; color becoming closer to N200A and 200B with development. Inner surface: Close to 56D; colors and patterns on outer surface visible on inner surface.

Leaf description:

*Arrangement and type*.—Alternate; simple; fancy-type.

*Length, shade house-grown potted plants*.—When tubers are de-eyed, about 17 cm to 19 cm; tubers not de-eyed, about 30 cm to 37 cm.

*Width, shade house-grown potted plants, flattened*.—When tubers are de-eyed, about 13 cm to 15 cm; tubers not de-eyed, about 14.5 cm to 26.5 cm.

*Shape*.—Broadly ovate; becoming slightly more obovate with development.

*Apex*.—Acute to acuminate.

*Base*.—Sagittate-peltate, cordate.

*Margin*.—Entire; mostly flat with broad undulations.

*Texture and luster, upper surface*.—Smooth, glabrous; dull sheen.

*Texture and luster, lower surface*.—Smooth, glabrous; areas surrounding the veins are slightly glaucous; dull sheen.

*Venation pattern*.—Pinnate and palmate.

*Color, shade house-grown potted plants*.—Fully developed leaves, upper surface: Background color: Close to 177A and 178A variably flushed with close to 139A, NN137A and 147A. Margins: Close to 187C. Basal notch: Close to 187C. Midvein and primary venation: Close to N186A and 202A; areas surrounding venation, close to 183B and 183C. Random spots and flecks: Close to 180D, 181D variably tinged with close to 186D. Fully developed leaves, lower surface: Background color: Close to 189A variably flushed with close to 200A; interveinal areas, close to 197B faintly tinged with close to 200A. Margins: Close to 187A and 187B. Basal notch: Close to 187B. Midvein: Close to 176B, 176C and 182D; areas surrounding midvein, variably tinged with close to N200A and 202A. Primary venation: Close to 196C and N200C occasionally tinged with close to 49C or N186A; areas surrounding midvein, variably tinged with close to 49D. Secondary venation: Close to N186C. Spots and flecks: Close to N155C, 49D and lighter than 63C.

*Petioles*.—Aspect: Initially upright and straight and leaning outwardly with development; flexible. Length, shade house-grown potted plants: When tubers are de-eyed, about 33 cm to 48 cm; tubers not de-eyed, about 50 cm to 62 cm. Diameter, distally, shade house-grown potted plants: When tubers are de-eyed, about 4 mm; tubers not de-eyed, about 4 mm to 7.5 mm. Diameter, proximally, shade house-grown potted plants: When tubers are de-eyed, about 5 mm to 7 mm; tubers not de-eyed, about 10 mm. Texture and luster: Smooth, glabrous; dull sheen. Color, shade house-grown potted plants: Close to between 203A and N200A; just below the leaf junction, close to 203A and 181B occasionally striped with close to 182D. Wing length, shade house-grown potted plants: About 9 cm to 12 cm. Wing diameter, shade house-grown potted plants: About 1 cm to 1.2 cm. Texture and luster, inner and outer surfaces: Smooth, glabrous; dull to slightly glossy. Wing color, shade house-grown potted plants: Outer surface: Close to N155B stippled and streaked with close to 200A. Timer surface: Close to N155A and 156D with small veins, close to N186B and lateral lobes flushed with close to 203A; colors and patterns on the outer surface are visible on the inner surface.

Inflorescence description: Inflorescences observed on ten week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet; jasmine-like with mint note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 11.7 cm. Length, distal open portion: About 8.2 cm. Length, proximal closed portion: About 3.5 cm. Width, distal open portion: About 2.2 cm. Depth, distal open portion: About 2.2 cm. Width, at constriction: About 1 cm. Width, proximal closed portion: About 1.7 cm. Shape, open portion: Narrowly elliptic. Apex: Acute to acuminate. Base: Acute. Margin: Entire; slightly recurved. Texture and luster, front surface: Smooth, glabrous; dull sheen. Texture and luster, rear surface: Smooth, glabrous; slightly glaucous and dull sheen. Color, front surface: Distal open portion: Close to 155C and 157C; with development, color becoming closer to 199A. Proximal closed portion: Close to 138C and 157C; towards the base, streaked and flecked with close to 187A; color does not change with development. Color, rear surface: Distal open portion: Close to 157C mottled with close to 145C; at the center, streaks and stripes, close to 183B and 183C; color does not change with development. Proximal closed portion: Close to 147C, 146B and 146C variably mottled with close to 183B, 183C and 184D; color does not change with development.

*Spadix*.—Length, overall: About 6.5 cm. Length, male flower zone: About 4.1 cm. Length, sterile zone: About 1.1 cm. Length, female flower zone: About 1.3 cm. Diameter, male flower zone: About 8 mm. Diameter, sterile flower zone: About 5 mm. Diameter, female flower zone: About 7 mm. Shape: Columnar, spindle-shaped. Apex: Blunt, rounded. Base: Obtuse. Aspect: Upright. Color, mature, male zone: Close to 158D. Color, mature, sterile zone: Close to 158D. Color, mature, female zone: Close to 159D and 13D. Male flowers: Quantity per spadix: About 95. Shape: Obovate. Height: About 3 mm. Diameter: About 3.5 mm. Pollen amount: Abundant. Pollen color: Close to 11C. Female flowers: Quantity per spadix: About 70. Shape: Ovate to elliptic. Height: About 2.5 mm. Diameter: About 2 mm. Stigma color: Close to 159D. Ovary color: Close to 13D.

*Scape*.—Length: About 32.8 cm. Diameter: About 6 mm. Strength: Sturdy; flexible. Aspect: Mostly erect, straight. Texture and luster: Smooth, glabrous; distally, slightly glaucous; dull sheen. Color: Close to 200B densely stippled and streaked with close to 200A; just below spathe, glaucous and close to 177C to 177D stippled and streaked with close to 200B to 200C.

*Seeds and fruits*.—To date, seed and fruit development have not been observed on plants of the new *Caladium*.

Pathogen tolerance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RFL THAI OF13-1055' as illustrated and described.

* * * * *